United States Patent [19]

Carr et al.

[11] Patent Number: 4,870,083

[45] Date of Patent: Sep. 26, 1989

[54] 1,4-DISUBSTITUTED-PIPERIDINYL COMPOUNDS USEFUL AS ANALGESICS AND MUSCLE RELAXANTS

[75] Inventors: Albert A. Carr; Thaddeus R. Nieduzak, both of Cincinnati; Francis P. Miller, Loveland; Stephen M. Sorensen, Cincinnati, all of Ohio

[73] Assignee: Merrell Dow Pharmaceuticals Inc., Cincinnati, Ohio

[21] Appl. No.: 254,208

[22] Filed: Oct. 11, 1988

Related U.S. Application Data

[63] Continuation-in-part of Ser. No. 124,692, Nov. 24, 1987, abandoned.

[51] Int. Cl.$^4$ .................. A61K 31/445; C07D 211/20; C07D 211/32; C07D 211/34
[52] U.S. Cl. .................................... 514/317; 546/236; 546/237; 546/238; 546/239; 546/240
[58] Field of Search ............... 546/236, 237, 238, 240, 546/239; 514/317

[56] References Cited

U.S. PATENT DOCUMENTS

| | | | |
|---|---|---|---|
| 3,852,455 | 12/1974 | Carr | 424/267 |
| 3,888,867 | 6/1975 | Carr | 260/293.8 |
| 3,895,030 | 7/1975 | Lafon | 260/326.5 J |
| 4,101,662 | 7/1978 | Ward et al. | 424/267 |
| 4,711,899 | 12/1987 | Gaudilliere et al. | 514/330 |

FOREIGN PATENT DOCUMENTS

| | | |
|---|---|---|
| 0034527 | 6/1965 | Japan . |
| 0532474 | 1/1978 | Japan . |
| 0217335 | 6/1984 | Japan . |
| 0612662 | 1/1986 | Japan . |
| 0227565 | 3/1987 | Japan . |

OTHER PUBLICATIONS

Derwent Patent Abstract No. 84-083570/14 (Abst. of E.P. Application 0,103,830) (1982).
Derwent Patent Abstract No. 84-076585/13 (Abst. of German Pat. Application 3234-995-A) (1982).
Derwent Pat. Abstract No. 00081x/01 (Abst. of Belgian Patent Application 832-036) (1974).
Derwent Pat. Abstract No. 75-10149w (Abst. of Netherlands Patent application No. 7409-752) (1973).
Derwent Abstract of granted Jap. Pat. No. 6024-388-B.

Primary Examiner—Glennon H. Hollrah
Assistant Examiner—Peter G. O'Sullivan
Attorney, Agent, or Firm—J. Michael Dixon

[57] ABSTRACT

The present invention relates to 1,4-disubstituted-piperidinyl compounds and their use as analgesic agents and as muscle relaxants.

34 Claims, No Drawings

1,4-DISUBSTITUTED-PIPERIDINYL COMPOUNDS USEFUL AS ANALGESICS AND MUSCLE RELAXANTS

This application is a continuation-in-part Ser. No. 07/124,694, filed Nov. 24, 1987, now abandoned.

The present invention relates to 1,4-disubstituted-piperidinyl compounds which are useful as analgesics and muscle relaxants. Another aspect of the invention relates to methods for relieving pain. A further aspect of the present invention relates to methods for relieving muscle spasms.

A wide number of compounds are currently available which possess therapeutic activity as analgesics. Unfortunately, most of the more potent analgesics are narcotics. Narcotics are potentially addictive and therefore are prone to abuse by susceptible individuals.

There are also a large number of compounds available which are capable of relieving muscle spasms. Most of these compounds have the undesirable side effect of sedating the patient and impairing his motor skills.

Thus, it would be a valuable contribution to the art to develop potent analgesics which are non-narcotic and therefore devoid of abuse potential.

It would also be a valuable contribution to the art to develop muscle relaxants which do not sedate the patient or impair his motor skills.

It is an object of the present invention to develop compounds possessing therapeutic activity as analgesics and muscle relaxants which possess the advantages described above.

It is a further object of the present invention to develop methods for relieving pain which are also devoid of abuse potential.

It is also an object of the present invention to develop methods for relieving muscle spasms which neither sedate the patient nor impair his motor skills.

Other aspects and objects of the present invention will become apparent hereinafter.

In accordance with the present invention, Applicants have discovered a new class of compounds which are useful as analgesics and as muscle relaxants. These compounds may be represented by the formula:

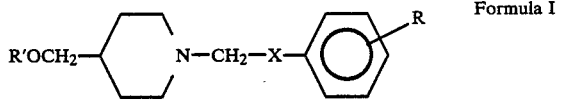

Formula I wherein; R' is selected from the group consisting of hydrogen, a lower alkanoyl having from 2-4 carbon atoms, and a benzyl group optionally substituted at positions 2-6 of the phenyl ring with at least one halogen; X is represented by a hydroxymethylene group or a carbonyl group; R is at least one group selected from the group consisting of halogens, lower alkyl groups, and lower alkoxy groups, with the proviso that the phenyl ring adjacent to the X substituent, is always (a) substituted with at least one fluorine atom, or (b) disubstituted at the 2 and 4 positions with a substituent selected from the group consisting of lower alkyl groups and lower alkoxy groups; or a pharmaceutically acceptable acid addition salts thereof. As used in this application:

(a) the term hydroxymethylene group refers to the following structure —CHOH—;

(b) the term carbonyl group refers to a structure corresponding to

(c) the term halogen refers to a fluorine, chlorine or bromine atom;

(d) the term lower alkyl group refers to a branched or straight chained alkyl group containing from 1-4 carbon atoms, such as methyl, ethyl, n-propyl, isopropyl, n-butyl and isobutyl;

(e) the term lower alkoxy group refers to a straight or branched alkoxy group containing from 1-4 carbon atoms, such as methoxy, ethoxy, n-propoxy, isopropoxy, n-butoxy and isobutoxy;

(f) the terms acyl and lower alkanoyl refer to the following structure

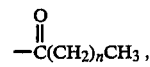

wherein n is an integer from 0-2;

(g) the term benzyl refers to a structure corresponding to:

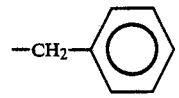

The expression "pharmaceutically acceptable acid addition salts" is intended to apply to any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic and sulfonic acids such as methane sulfonic acid, 2-hydroxyethane sulfonic acid, and p-toluene sulfonic acid.

Some of the compounds of the present invention exhibit optical activity. Any reference in this application to the compounds of the present invention is meant to encompass either a specific stereoisomer or a mixture of stereo-isomers.

In order for the compounds of the present invention to exhibit the above described therapeutic utilities; it is necessary that the phenyl ring adjacent to the X substituent, always be: (a) substituted with at least one fluorine atom, or (b) disubstituted at the 2 and 4 positions with a substituent selected from the group consisting of lower alkyl groups, and lower alkoxy groups.

Examples of suitable non-narcotic analgesics and non-sedative muscle relaxants which are represented by Formula I are those selected from the group consisting of:

(1) α-(4-fluorophenyl)-4-(hydroxymethyl)-1-piperidine-ethanol;
(2) α-(2,4-dimethylphenyl)-4-(hydroxymethyl)-1-piperidine-ethanol;
(3) 1-(4-fluorophenyl)-2-[4-(hydroxymethyl)-1-piperidinyl]-ethanone;
(4) 1-(2,4-dimethylphenyl)-2-[4-(hydroxymethyl)-1-piperidinyl]-ethanone,
(5) 1-(4-fluorophenyl)-2-[4-[(1-oxopropoxy)methyl]-1-piperidinyl]-ethanone;
(6) 1-(2,4-dimethylphenyl)-2-[4-[(1-oxopropoxy)methyl]-1-piperidinyl]-ethanone;
(7) 1-(4-fluorophenyl)-2-[4-(benzyloxymethyl)-1-piperidinyl]-ethanone;
(8) α-(4-fluorophenyl)-4-(benzyloxymethyl)-1-piperidineethanol;
(9) 1-(4-fluorophenyl)-2-[4-(4-fluorobenzyloxymethyl)-1-piperidinyl]-ethanone, and;
(10) α-(4-fluorophenyl)-4-(4-fluorobenzyloxymethyl)-1-piperidineethanol.

The currently preferred compounds of the present invention are those wherein the phenyl ring adjacent to the X substituent, is monosubstituted with a fluorine atom. The most preferred compounds of the present invention are those wherein the monosubstituted fluorine atom is located at the 4 position of the phenyl ring which is adjacent to the X substituent.

Representative examples of the most preferred compounds of the present invention are those selected from the group consisting of α-(4-fluorophenyl)-4-(hydroxymethyl)-1-piperidineethanol, 1-(4-fluorophenyl)-2-[4-(hydroxymethyl)-1-piperidinyl)-ethanone, and 1-(4-fluorophenyl)-2-[4-[(1-oxopropoxy)methyl]-1-piperidinyl]-ethanone.

The compounds of the present invention can be prepared by techniques known to those skilled in the art. A novel and currently preferred manner of preparing these compounds is described below.

If the desired compound is a 1,2-disubstituted ethanone (i.e., where X is a carbonyl group as defined in Formula I) then the following synthesis is preferred.

Starting materials are a 4-substituted piperidine as described in Formula II, wherein R' is as defined in Formula I; and a 2-halo-substituted acetophenone as described in Formula III, wherein R is as defined in Formula I and Y is a halogen, preferably chlorine.

Formula II

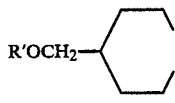

Formula III

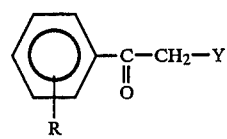

The 4-substituted piperidine should correspond structurally to its counterpart in the desired 1,2-disubstituted ethanone, since all of its substituents will be retained in the final product. Likewise, the 2-halo-substituted acetophenone should correspond structurally to its counterpart in the desired 1,2-disubstituted ethanone, since all of its substituents with the exception of the halogen atom at the Y position will be retained in the final product.

For example, if the desired compound is 1-(4-fluorophenyl)-2-[4-(hydroxymethyl)-1-piperidinyl]-ethanone then the preferred starting materials are: (a) 4-hydroxymethylpiperidine and, (b) 2-chloro-4'-fluoroacetophenone.

If the preferred starting material of Formula II is unavailable (i.e. a 4-substituted piperidine wherein R' corresponds structurally to its counterpart in the desired 1,2-disubstituted ethanone); then R' can be added to the structure after the 1,2-disubstituted ethanone is formed. This can be accomplished by techniques known in the art.

It is currently preferred that approximately equimolar concentrations of the 4-substituted piperidine and the 2-halo-substituted-acetophenone be utilized in the synthesis. A slight excess of either of the reactants is not deleterious to the synthesis.

It is also preferred that the reaction be conducted in the presence of either an organic or inorganic base. Triethylamine is currently preferred. The base is preferably present in a molar excess relative to the 4-substituted piperidine.

It is also preferred that the reaction be conducted in the presence of an alkaliiodo catalyst. Sodium iodide is currently preferred. The alkaliiodo catalyst is preferably present in a quantity of from 0.1 to 1 mol percent based upon the quantity of 4-substituted-piperidine present in the reaction zone.

The 4-substituted piperidine and the 2-halo-substituted acetophenone are preferably stirred together for a period of time ranging from 1 to 30 hours. It is preferred that the reaction be conducted at a temperature range of from 25° to 115° C. It is also preferred that the reaction be conducted in an organic solvent. Representative examples of suitable solvents include dichloromethane, methanol, tetrahydrofuran, toluene, or chloroform, and the like.

The 1,2-disubstituted ethanone produced above can be recovered from the reaction zone by techniques known in the art. One suitable technique is to extract the reaction zone with an organic solvent, after water has been added to the reaction. The desired 1,2-disubstituted ethanone will be found in the organic phase.

The 1,2-disubstituted ethanone can then be purified by techniques known in the art. One such suitable technique is Representative examples of suitable solvent systems which are currently being utilized include methanol/2-butanone, methanol/ethyl acetate, chloroform/benzene and ethyl acetate/hexanes if the desired compound is present as an acid addition salt. Chloroform/benzene, methanol/water and ethyl acetate/hexanes are representative examples of suitable solvent systems currently being utilized if the desired compound is present as a free base. Other appropriate solvent systems known to those skilled in the art could also be utilized.

If the desired compound is a 1,2-disubstituted ethanol (i.e., X in Formula I is a hydroxymethylene group) then the following synthesis is preferred.

A 1,2-disubstituted ethanone corresponding structurally to the desired 1,2-disubstituted ethanol should be prepared in the manner previously disclosed. The carbonyl group located at the 1-carbon of the 1,2-disubstituted ethanone may be reduced to an alcohol, which then produces the desired 1,2-disubstituted ethanol.

For example, reduction of the 1,2-disubstituted ethanone, 1-(4-fluorophenyl)-2-[4-(hydroxymethyl)-1-piperidinyl]-ethanone produces α-(4-fluorophenyl)-4-(hydroxymethyl)-1-piperidineethanol.

The reduction of the 1,2-disubstituted ethanone may be carried out with a variety of reducing agents as known to those skilled in the art. Lithium aluminum hydride and sodium borohydride are representative examples of suitable reducing agents. Lithium aluminum hydride is currently utilized.

The reducing agent is preferably present in the reaction zone in a molar excess relative to the quantity of 1,2-disubstituted ethanone present and more preferably, is present in the molar ratio of from 2–4 moles of reducing agent for every mole of 1 ethanone utilized.

It is currently preferred that the reduction be conducted at a temperature range of from 0° to 25° C. and for a period of time ranging from 1 to 24 hours. It is also currently preferred that the reaction be conducted in an organic solvent. Representative examples of suitable solvents include tetrahydrofuran or ether. Methanol is suitable for use with sodium borohydride.

After the reduction is completed, it is preferred that the reaction be quenched by the addition of water.

The 1,2-disubstituted ethanol may then be recovered from the reaction zone by numerous techniques as known to those skilled in the art. The 1,2-disubstituted ethanol can be recovered by extraction with an organic solvent after water has been added to the reaction zone. Alternatively, the 1,2-disubstituted ethanol can be recovered by filtration.

The 1,2-disubstituted ethanol may be purified by numerous techniques as known to those skilled in the art. One such suitable technique is recrystallization from a suitable solvent system. Representative examples of suitable solvent systems currently being utilized include methanol/2-butanone, methanol/ethyl acetate, chloroform/benzene and ethyl acetate/hexanes if the desired compound is present as an acid addition salt. Chloroform/benzene, methanol/water and ethyl acetate/hexanes are representative examples of suitable solvent systems currently being utilized if the desired compound is present as a free base. Other appropriate solvent systems known to those skilled in the art could also be utilized.

As noted supra, the compounds described by Formula I may be utilized as analgesics. The compounds possess a level of potency sufficient to inhibit the sensation of the severe levels of pain that are commonly associated with conditions such as metastatic carcinoma, myocardial infarctions or traumatic injuries.

Despite this high level of potency, the compounds are non-narcotic. This means that they are devoid of the abuse potential that accompanies most analgesics.

One manner of demonstrating the analgesic utility of these compounds is to conduct the following test protocol.

From 5 to 10 mice, should be administered from 0.1 to 200 mg/kg of the compound either subcutaneously or intragastrically. Thirty minutes after the administration of the test compound, the mice should be administered 0.4 ml of a 0.25% v/v solution of acetic acid intraperitoneally.

Five minutes after the administration of the acetic acid, the mice should be observed for signs of squirming and writhing which is indicative of pain.

A compound is considered to posses significant analgesic activity if the mice which are administered said compound do not exhibit signs of pain during the test (i.e. squirming and writhing).

One manner of demonstrating the non-narcotic properties of these compounds is the following test protocol.

Three mice should be administered up to 800 mg/kg of the desired compound subcutaneously. Thirty minutes later the mice should be placed upon a hot plate which has been heated to a temperature of 55° C.

A compound is considered to be non-narcotic if the mice jump within the first 20 seconds of when they are initially placed upon the hot plate.

One manner of demonstrating the utility of these compounds as muscle relaxants; is by their ability to antagonize the sustained contraction of the sacrococcygeus dorsalis muscle in mice, which the administration of morphine typically causes (Straub Tail Test). This may be demonstrated in the following manner.

From 5 to 10 mice should be administered from 0.1 to 200 mg/kg of the compound. Thirty minutes later the mice should be administered 60 mg/kg of morphine subcutaneously.

The mice should be observed for 30 minutes after the administration of the morphine in order to determine whether the test compound has blocked the ability of morphine to cause the sustained contraction of the sacrococcygeus dorsalis muscle in the mice. Contraction of this muscle causes the tail of the mice to be elevated at an angle of at least 90° C. Thus if a compound is a muscle relaxant, the tail of the mice will not be elevated.

One manner of demonstrating that the compounds of the present invention do not impair motor skills or cause sedation is the following test protocol.

Mice are initially screened for use in the test by placing them on a horizontal rod which is rotating at 15 rpm. Those mice which fall off during a 120 second interval are excluded from further testing.

The mice satisfying the criterion described above are then administered up to 800 mg/kg either subcutaneously or intragastrically of the test compound.

Thirty minutes later the mice are placed back upon the rotating horizontal bar and observed for 90 seconds.

In order to determine if the compound is non-sedative and does not impair motor skills, it is necessary to interpret the results of this test in light of the $ED_{50}$ obtained in the Straub Tail test noted supra. A compound is considered to be non-sedative and to not impair motor skills, if the ratio between the dose at which approximately one-half of the mice fall off the rotating rod and the dose at which approximately one-half of the mice did not experience morphine induced contraction of the sacrococcygeus dorsalis muscle is about 2:1 or greater.

The compounds of the present invention may be administered by a variety of routes. They are effective if administered orally. The compounds may also be administered parenterally (i.e. subcutaneously, intravenously, intramuscularly, or intraperitoneally).

It is currently preferred that the compounds are administered parenterally. The quantity of the compound administered will vary depending on the patient, the mode of administration, and the severity of the condition that is being treated. Repetitive daily administration of the compounds may be desired and will vary with patient condition and mode of administration.

Although the dosage required will vary from patient to patient, it is generally preferred that the compounds of the present invention be administered within a dosage range of from 0.1-200 mg/kg of patient body weight/day whether being administered orally or parenterally. This dosage range is applicable whether the compounds are being utilized as an analgesic or as a muscle relaxant.

As used in this application, the term patient refers to a warm-blooded animal. Thus, the compounds are effective for the relief of pain and muscle spasms in birds, such as chickens and turkeys; or mammals, such as humans, primates, sheep, horses, cattle, pigs, dogs, cats, rats, and mice, etc.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

The following examples are presented in order to further illustrate the present invention. However, they should not be construed as limiting the scope of the invention in any manner.

EXAMPLE 1

The purpose of this example is to demonstrate one manner of preparing the compound, 1-(4-fluorophenyl)-2-[4-(hydroxymethyl)-1-piperidinyl]-ethanone hydrochloride.

To a solution of 4.0 g (34.8 mmol) of 4-hydroxymethyl piperidine in 150 ml of tetrahydrofuran was added 9.6 ml (69.6 mmol) of triethylamine, 6.5 g (38.3 mmol) of 2-chloro-4'-fluoroacetophenone and a catalytic amount of sodium iodide. The reaction mixture was stirred at room temperature for 24 hours. After stirring, the reaction mixture was poured into a saturated solution of aqueous sodium bicarbonate. The solution was then extracted with ethyl acetate and the resulting organic layer was separated.

The organic layer was then dried with magnesium sulfate, filtered, and concentrated on a rotary evaporator. The resulting thick red oil was then diluted with methylene chloride and gaseous hydrogen chloride was bubbled through the solution. This mixture was then concentrated on a rotary evaporator. The 1-(4-fluorophenyl)-2-[4-(hydroxymethyl)-1-piperidinyl]-ethanone hydrochloride was purified by recrystallization from a solvent system containing methanol and 2-butanone. 7.18 g (25 mmol) of the desired product was obtained which had a melting point of 250° C.

EXAMPLE 2

The purpose of this example is to demonstrate a manner of preparing a compound of the present invention, wherein the desired substituent on the 4-substituted piperidinyl ring (i.e., R') is not readily available as a starting material. In such a situation, the substituent can be added after the 1,2-disubstituted ethanone has been formed.

The desired compound in this situation is 1-(4-fluorophenyl)-2-[4-[(1-oxypropoxy)methyl]-1-piperidinyl]-ethanone. However, 4-(1-oxopropoxy)methylpiperidine was not available as a starting material. Therefore, the desired 1,2-disubstituted ethanone was formed in the following manner.

2.3 g (8.0 mmol) of 1-(4-fluorophenyl)-2-[4-(hydroxymethyl)-1-piperidinyl]-ethanone was prepared in the manner disclosed in Example I.

This material was then dissolved in 200 ml of tetrahydrofuran. To this solution was added 1.6 g (12.0 mmol) of propionic anhydride, 5 g (59 mmol) of sodium bicarbonate, and a catalytic amount of 4-dimethylaminopyridine. This mixture was then stirred at room temperature for 24 hours.

The reaction mixture was then admixed with distilled water. The resulting solution was then extracted with ethyl acetate.

The organic layer obtained above was separated and then washed with a 10% w/w solution of aqueous hydrogen chloride. The resulting aqueous layer was separated and neutralized with solid sodium bicarbonate. This solution was then extracted with ethyl acetate and the resulting organic layer was saved.

The organic layer was then dried with magnesium sulfate, filtered and gaseous hydrogen chloride was bubbled through the resulting filtrate.

The product, 1-(4-fluorophenyl)-2-[4-[(1-oxypropoxy)methyl]-1-piperidinyl]-ethanone hydrochloride was recovered by recrystallization from a solvent system containing chloroform and benzene.

1.1 g (3.2 mmol) of 1-(4-fluorophenyl)-2-[4-[(1-oxypropoxy)methyl]-1-piperidinyl]-ethanone hydrochloride was obtained which had a melting point of 170°–174° C.

EXAMPLE 3

The purpose of this example is to demonstrate a manner of preparing a 1,2-disubstituted ethanol compound in accordance with the present invention. This was accomplished in the following manner.

First, the 1,2-disubstituted ethanone, 1-(4-fluorophenyl)-2-[4-(carbomethoxy)-1-piperidinyl]-ethanone hydrochloride was prepared. This was accomplished in the following manner.

To a suspension of 20 g (112 mmol) of 4-carbomethoxypiperidine hydrochloride which was suspended in 300 ml of methylene chloride was added 30 gm (357 mmol) of sodium bicarbonate followed by 21.1 g (123 mmol) of 2-chloro-4'-fluoroacetophenone.

This mixture was refluxed for 24 hours at 40° C. After refluxing, the reaction mixture was poured into distilled water and extracted with methylene chloride.

The organic layer was then separated, dried with magnesium sulfate, filtered and concentrated on a rotary evaporator.

The resulting concentrate was added to a solution of methanolic hydrogen chloride.

The 1,2-disubstituted ethanone, 1-(4-fluorophenyl)-2-[4-(carbomethoxy)-1-piperidinyl]-ethanone hydrochloride was purified by recrystallization from a methanol/2-butanone solvent system. 23.2 g (73.6 mmol) of the desired product was obtained which had a melting point of 170° C.

10 g of this product was then reduced in order to produce the desired 1,2-disubstituted ethanol, α-(4-fluorophenyl)-4-(hydroxymethyl)-1-piperidineethanol. This reduction was accomplished in the following manner.

10.0 g (31.7 mmol) of the 1,2-disubstituted ethanone, 1-(4-fluorophenyl)-2-[4-(carbomethoxy)-1-piperidinyl]-ethanone hydrochloride, was mixed in 500 ml of tetrahydrofuran. The suspension was cooled to 0° C. and 4.8 g (127 mmol) of lithium aluminum hydride was added as a solid over approximately 15 minutes. The solution was stirred for 15 hours at room temperature and then the reaction mixture was cooled to 0° C. and treated with 30 ml of water.

This mixture was then stirred for 30 minutes at room temperature and then filtered. After filtration, it was dried with magnesium sulfate, filtered, and concentrated on a rotary evaporator.

The concentrate obtained above was then placed in a solvent system composed of methanol and water and subjected to recrystallization.

7.0 g (27.7 mmol) of α-(4-fluorophenyl)-4-(hydroxymethyl)-1-piperidineethanol was obtained which had a melting point of 113° C.

EXAMPLE 4

The purpose of this example is to demonstrate a method for preparing a compound according to Formula I wherein R' is represented by a substituted benzyl group.

To a solution of 20.0 g (150 mmole) of isonipecotic acid in 200 ml of water were added 20.0 g (190 mmole) of sodium carbonate and 37.2 g (170 mmol) of di-t-butyl dicarbonate. The suspension was stirred for 24 hours at room temperature and extracted with ether. The aqueous layer was acidified to pH≈4 with aqueous 10% hydrogen chloride and extracted with ethyl acetate. The organic layer was dried with magnesium sulfate and concentrated to yield 31.4 g of 4-carboxy-piperidine-1-carboxylic acid t-butyl ester as a white solid with melting point 146°-150° C.

To a 0° C. solution of 15.0 g (65.5 mmole) of the 4-carboxy-piperidine-1-carboxylic acid-t-butyl ester produced above, in 200 ml of dry tetrahydrofuran, under nitrogen gas, was added 98.2 ml (98.2 mmole) of 1.0 M borane in tetrahydrofuran over 10 minutes. The reaction mixture was stirred an additional 4 hours at room temperature, quenched with 500 ml of aqueous saturated sodium bicarbonate and extracted with ethyl acetate. The organic layer was dried with magnesium sulfate and concentrated to give 14.1 g of 4-hydroxymethyl-piperidine-1-carboxylic acid t-butyl ester as a white solid with melting point 75°-76° C.

To a solution of 5.0 g (23.2 mmole) of the 4-hydroxymethyl-piperidine-1-carboxylic acid t-butyl ester produced above, in 100 ml of dimethylformamide, was added 1.2 g (25.6 mmole) of a 50% sodium hydride oil dispersion. After stirring for 0.5 hours, 5.0 g (34.9 mmole) of 4-fluorobenzyl chloride was added, followed by a catalytic amount of tetrabutylammonium iodide. The suspension was stirred an additional 24 hours, quenched with saturated aqueous sodium chloride and extracted with ether. The organic layer was dried with magnesium sulfate and concentrated. The resulting oil was treated with methanolic hydrogen chloride for 4 hours. A white solid was obtained upon concentration, which was filtered and washed with hexane. 5.1 g of 4-(4-fluoro-benzyloxymethyl)-piperidine hydrochloride was obtained which had a melting point of 142°-145° C.

To a solution of 1.4 g (6.3 mmole) of the 4-(4-fluorobenzyloxymethyl)-piperidine produced above, in 125 ml of methanol, was added 1.3 g (12.6 mmole) of triethylamine and 1.4 g (9.4 mmole) of 2-chloro-4-fluoroacetophenone. After 24 hours at room temperature, the reaction mixture was diluted with saturated aqueous sodium bicarbonate and extracted with chloroform. The organic layer was dried with magnesium sulfate and concentrated. The residue was chromatographed on silica gel using 30% ethyl acetate hexanes as eluent. The resulting oil was isolated as its hydrochloride salt which was recrystallized from ethyl acetate to give 0.90 g of 1-(4-fluorophenyl)-2-[4-(4-fluorobenzyloxymethyl)-1-piperidinyl]-ethanone hydrochloride as a white solid with a melting point of 155°-158° C.

What is claimed is:

1. A compound of the formula:

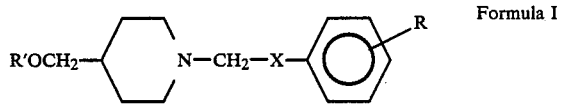

Formula I wherein; R' is selected from the group consisting of hydrogen, a lower alkanoyl having from 2-4 carbon atoms, and a benzyl group, optionally substituted at positions 2-6 of the phenyl ring with at least one halogen atom; X is represented by a hydroxymethylene group or a carbonyl group; R is at least one group selected from the group consisting of halogens, lower alkyl groups, and lower alkoxy groups with the proviso that the phenyl ring adjacent to the X substituent is always: (a) substituted with at least one fluorine atom, or (b) disubstituted at the 2 and 4 positions with a substituent selected from the group consisting of lower alkyl groups and lower alkoxy groups; or a pharmaceutically acceptable acid addition salt thereof.

2. A compound according to claim 1, wherein R is represented by at least one fluorine atom.

3. A compound according to claim 1, wherein said compound is α-(4-fluorophenyl)-4-(hydroxymethyl)-1-piperidineethanol.

4. A compound according to claim 1, wherein said compound is α-(2,4-dimethylphenyl)-4-(hydroxymethyl)-1-piperidineethanol.

5. A compound according to claim 1, wherein said compound is 1-(4-fluorophenyl)-2-[4-[(1-oxopropoxy)-methyl]-1-piperidinyl]-ethanone.

6. A compound according to claim 1, wherein said compound is 1-( 2,4-dimethylphenyl)-2-[4-[(1-oxopropoxy)-methyl]-1-piperidinyl]-ethanone.

7. A compound according to claim 1, wherein said compound is 1-(4-fluorophenyl)-2-[4-(hydroxymethyl)-1-piperidinyl]-ethanone.

8. A compound according to claim 1, wherein said compound is 1-(2,4-dimethylphenyl)-2-[4-(hydroxymethyl)-1-piperidinyl]-ethanone.

9. A compound according to claim 1, wherein said compound is 1-(4-fluorophenyl)-2-[4-(benzyloxymethyl)-1-piperidinyl]-ethanone.

10. A compound according to claim 1, wherein said compound is α-(4-fluorophenyl)-4-(benzyloxymethyl)-1-piperidine ethanol.

11. A compound according to claim 1, wherein said compound is 1-(4-fluorophenyl)-2-[4-(4-fluorobenzyloxymethyl)-1-piperidinyl]-ethanone.

12. A compound according to claim 1, wherein said compound is α-(4-fluorophenyl)-4-(4-fluorobenzyloxymethyl)-1-piperidineethanol.

13. A method for relieving or reducing pain in a patient, comprising administering to said patient a compound of the formula:

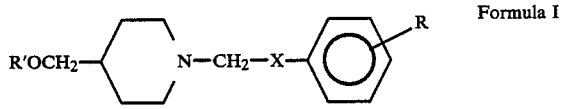

Formula I wherein; R' is selected from the group consisting of hydrogen, a lower alkanoyl having from 2-4 carbon atoms, and a benzyl group, optionally substituted at positions 2-6 of the phenyl ring with at least one halogen atom; X is represented by a hydroxymethylene group or a carbonyl group; R is at least one group selected from the group consisting of halogens, lower alkyl groups, and lower alkoxy groups with the proviso that the phenyl ring adjacent to the X substituent is always: (a) substituted with at least one fluorine atom, or (b) disubstituted at the 2 and 4 positions with a substituent selected from the group consisting of lower alkyl groups and lower alkoxy groups; or a pharmaceutically acceptable acid addition salt thereof, in a quantity sufficient to either reduce or relieve the sensation of pain.

14. A method according to claim 13, wherein said compound is α-(4-fluorophenyl)-4-(hydroxymethyl)-1-piperidineethanol.

15. A method according to claim 13, wherein said compound is α-(2,4 dimethylphenyl)-4-(hydroxymethyl)-1-piperidineethanol.

16. A method according to claim 13, wherein said compound is 1-(4-fluorophenyl)-2-[4-[(1-oxopropoxy)-methyl]-1-piperidinyl]-ethanone.

17. A method according to claim 13, 1-(2,4-dimethylphenyl)-2-[4-[(1-oxopropoxy)methyl]-1-piperidinyl]-ethanone.

18. A method according to claim 13, wherein said compound is 1-(4-fluorophenyl)-2-[4-(hydroxymethyl)-1-piperidinyl]-ethanone.

19. A method according to claim 13, wherein said compound is 1-(2,4-dimethylphenyl)-2-[4-(hydroxymethyl)-1-piperidinyl]-ethanone.

20. A method according to claim 13, wherein said compound is 1-(4-fluorophenyl)-2-[4-(benzyloxymethyl)-methyl]-1-piperidinyl]-ethanone.

21. A method according to claim 13, wherein said compound is α-(4-fluorophenyl)-4-(benzyloxymethyl)-1-piperidineethanol.

22. A method according to claim 13, wherein said compound is 1-(4-fluorophenyl)-2-[4-(4-fluorobenzyloxymethyl)-1-piperidinyl]-ethanone.

23. A method according to claim 13, wherein said compound is α-(4-fluorophenyl)-4-(4-fluorobenzyloxymethyl)-1-piperidineethanol.

24. A method for relieving or alleviating muscle spasms comprising administering to a patient a compound of the formula:

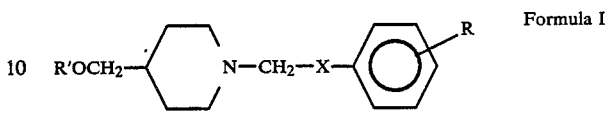

Formula I wherein; R' is selected from the group consisting of hydrogen, a lower alkanoyl having from 2-4 carbon atoms, and a benzyl group optionally substituted at positions 2-6 of the phenyl ring with at least one halogen atom; X is represented by a hydroxymethylene group or a carbonyl group; R is at least one group selected from the group consisting of halogens, lower alkyl groups, and lower alkoxy groups with the proviso that the phenyl ring adjacent to the X substituent is always: (a) substituted with at least one fluorine atom, or (b) disubstituted at the 2 and 4 positions with a substituent selected from the group consisting of lower alkyl groups and lower alkoxy groups; or a pharmaceutically acceptable acid addition salt thereof; in a quantity sufficient relieve or alleviate the spasm.

25. A method according to claim 24, wherein said compound is α-(4-fluorophenyl)-4-(hydroxymethyl)-1-piperidineethanol.

26. A method according to claim 24, wherein said compound is α-(2,4-dimethylphenyl)-4-(hydroxymethyl)-1-piperidineethanol.

27. A method according to claim 24, wherein said compound is 1-(4-fluorophenyl)-2-[4-[(1-oxopropoxy)-methyl]-1-piperidinyl]-ethanone.

28. A method according to claim 24, 1-(2,4-dimethylphenyl)-2-[4-[(1-oxopropoxy)methyl]-1-piperidinyl]-ethanone.

29. A method according to claim 24, wherein said compound is 1-(4-fluorophenyl)-2-[4-(hydroxymethyl)-1-piperidinyl]-ethanone.

30. A method according to claim 24, wherein said compound is 1-(2,4-dimethylphenyl)-2-[4-(hydroxymethyl)-1-piperidinyl]-ethanone.

31. A method according to claim 24, wherein said compound is 1-(4-fluorophenyl)-2-[4-(benzyloxymethyl)-1-piperidinyl]-ethanone.

32. A method according to claim 24, wherein said compound is α-(4-fluorophenyl)-4-(benzyloxymethyl)-1-piperidineethanol.

33. A method according to claim 24, wherein said compound is 1-(4-fluorophenyl)-2-[4-(4-fluorobenzyloxymethyl)-1-piperidinyl]-ethanone.

34. A method according to claim 24, wherein said compound is α-(4-fluorophenyl)-4-(4-fluorobenzyloxymethy-1-piperidineethanol.

* * * * *